(12) United States Patent
Beswick et al.

(10) Patent No.: US 8,450,314 B2
(45) Date of Patent: May 28, 2013

(54) PYRIMIDOPYRIDAZINE DERIVATIVES USEFUL AS P38 MAPK INHIBITORS

(75) Inventors: Amanda Beswick, Harlow (GB); Bohdan Waszkowycz, Harlow (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/201,534

(22) PCT Filed: Feb. 16, 2010

(86) PCT No.: PCT/GB2010/050256
§ 371 (c)(1),
(2), (4) Date: Dec. 19, 2011

(87) PCT Pub. No.: WO2010/094955
PCT Pub. Date: Aug. 26, 2010

(65) Prior Publication Data
US 2012/0077809 A1    Mar. 29, 2012

(30) Foreign Application Priority Data

Feb. 17, 2009    (GB) .................................. 0902648.5

(51) Int. Cl.
*A61K 31/535* (2006.01)
*C07D 413/12* (2006.01)
*C07D 413/14* (2006.01)

(52) U.S. Cl.
USPC ..................... 514/234.2; 514/236.5; 544/117; 544/131

(58) Field of Classification Search
CPC ..... C07D 413/14; C07D 413/12; A61K 31/535
USPC ..................... 544/117, 131; 514/234.2, 236.5
See application file for complete search history.

(56) References Cited

FOREIGN PATENT DOCUMENTS

| WO | 98 27098 | 6/1998 |
| WO | 00 17204 | 3/2000 |
| WO | 2009 015000 | 1/2009 |

OTHER PUBLICATIONS

International Search Report issued Apr. 29, 2010 in PCT/GB10/50256 filed Feb. 16, 2010.

*Primary Examiner* — Rebecca Anderson
(74) *Attorney, Agent, or Firm* — Oblon, Spivak, McClelland, Maier & Neustadt, L.L.P.

(57) ABSTRACT

A compound formula (IA) or (IB), or a pharmaceutically acceptable thereof; wherein the substituents are defined as in the claims, and their use as P38 MAP kinase.

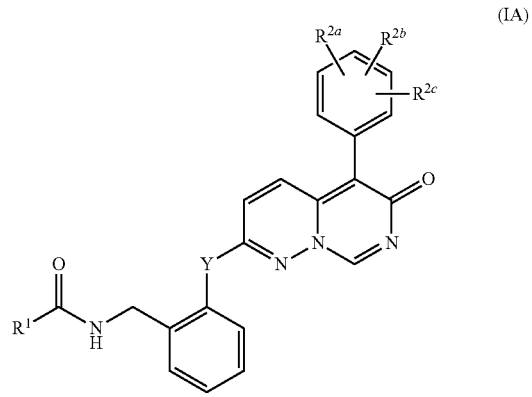

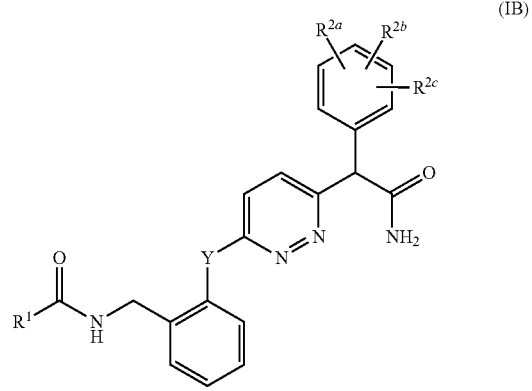

20 Claims, No Drawings

PYRIMIDOPYRIDAZINE DERIVATIVES USEFUL AS P38 MAPK INHIBITORS

This invention relates to compounds and compositions that are p38 MAPK inhibitors, useful as anti-inflammatory agents in the treatment of, inter alia, diseases of the respiratory tract.

BACKGROUND TO THE INVENTION

Mitogen activated protein kinases (MAPK) constitute a family of proline-directed serine/threonine kinases that activate their substrates by dual phosphorylation. There are four known human isoforms of p38 MAP kinase, p38α, p38α, p38γ and p38δ. The p38 kinases, which are also known as cytokine suppressive anti-inflammatory drug binding proteins (CSBP), stress activated protein kinases (SAPK) and RK, are responsible for phosphorylating (Stein et al., Ann. Rep. Med. Chem., 1996, 31, 289-298) and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) (Herlaar E. & Brown Z., Molecular Medicine Today, 1999, 5, 439-447). The products of p38 phosphorylation have been shown to mediate the production of inflammatory cytokines, including tumor necrosis factor alpha (TNF α), interleukin-(IL-)-1, and cyclooxygenase-2 (COX-2). IL-1 and TNFα are also known to stimulate the production of other proinflammatory cytokines such as IL-6 and IL-8.

IL-1 and TNFα are biological substances produced by a variety of cells, such as monocytes or macrophages. IL-1 has been demonstrated to mediate a variety of biological activities thought to be important in immunoregulation and other physiological conditions such as inflammation (e.g. Dinarello et al., Rev. Infect. Disease, 1984, 6, 51). Excessive or unregulated TNF production (particularly TNFα) has been implicated in mediating or exacerbating a number of diseases, and it is believed that TNF can cause or contribute to the effects of inflammation in general. IL-8 is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes and basophils. Increase in IL-8 production is also responsible for chemotaxis of neutrophils into the inflammatory site in vivo.

Inhibition of signal transduction via p38, which in addition to IL-1, TNF and IL-8 described above is also required for the synthesis and/or action of several additional pro-inflammatory proteins (e.g., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for p38 kinase inhibitors (Badger et al., J. Pharm. Exp. Thera., 1996, 279, 1453-1461; Griswold et al, Pharmacol. Comm., 1996, 7, 323-229). In particular, p38 kinase inhibitors have been described as potential agents for treating rheumatoid arthritis. In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α IL-1β, IL-6, IL-4, IL-5 and IL-13 (Haddad et al, Br. J. Pharmacol., 2001, 132 (8), 1715-1724; Underwood et al, Am. J. Physiol. Lung Cell. Mol. 2000, 279, 895-902; Duan et al., 2005 Am. J. Respir. Crit. Care Med., 171, 571-578; Escott et al Br. J. Pharmacol., 2000, 131, 173-176; Underwood et al., J. Pharmacol. Exp. Ther. 2000, 293, 281-288). Furthermore, they significantly inhibit neutrophilia and the release of MMP-9 in LPS, ozone or cigarette smoke animal models. There is also a significant body of preclinical data highlighting the potential benefits of inhibition of the p38 kinase that could be relevant in the lung (Lee et al., Immunopharmacology, 2000, 47, 185-200). Thus, therapeutic inhibition of p38 activation may be important in the regulation of airway inflammation.

The implication of the p38MAPK pathway in various diseases has been reviewed by P. Chopra et al. (Expert Opinion on Investigational Drugs, 2008, 17(10), 1411-1425). It is believed that the compounds of the present invention can be used to treat p38 mediated diseases such as: asthma, chronic or acute bronchoconstriction, bronchitis, acute lung injury and bronchiectasis, pulmonary artery hypertension, tuberculosis, lung cancer, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, Crohn's disease, ophthalmic diseases, ophthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, eczema, disorders of the female reproductive system, pathological (but non-malignant) conditions, such as hemaginomas, angiofibroma of the nasopharynx, and avascular necrosis of bone, benign and malignant tumors/neoplasia including cancer, leukaemia, lymphoma, systemic lupus erthrematosis (SLE), angiogenesis including neoplasia, haemorrhage, coagulation, radiation damage, and/or metastasis. Chronic release of active TNF can cause cachexia and anorexia, and TNF can be lethal. TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV7), human herpesvirus-8 (HHV-8), pseudorabies and rhinotracheitis, among others.

Known P38 kinase inhibitors have been reviewed by G. J. Hanson (Expert Opinions on Therapeutic Patents, 1997, 7, 729-733) J Hynes et al. (Current Topics in Medicinal Chemistry, 2005, 5, 967-985), C. Dominguez et al (Expert Opinions on Therapeutics Patents, 2005, 15, 801-816) and L. H. Pettus & R. P. Wurtz (Current Topics in Medicinal Chemistry, 2008, 8, 1452-1467). P38 inhibitors containing the triazanaphthalenone ring system are known in the art, for example WO1998/027098.

SUMMARY OF THE INVENTION

The compounds of the present invention are inhibitors of p38 mitogen activated protein kinase ("p38 MAPK", "p38 kinase" or "p38"), including p38α kinase, and are inhibitors of cytokine and chemokine production including TNFα and IL-8 production. They have a number of therapeutic applications, in the treatment of inflammatory diseases, particularly allergic and non-allergic airways diseases, more particularly obstructive or inflammatory airways diseases such as chronic obstructive pulmonary disease ("COPD") and asthma. They are therefore particularly suited for pulmonary delivery, by inhalation by nose or mouth.

According to the invention there is provided a compound of formula (IA) or (IB), or a pharmaceutically acceptable salt thereof;

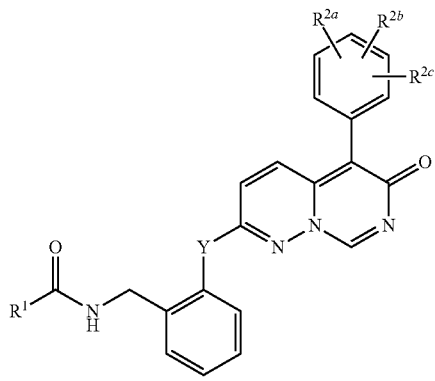
(IA)

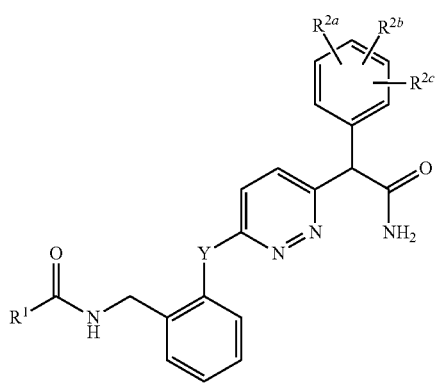
(IB)

wherein;
$R^{2a}$, $R^{2b}$, $R^{2c}$ are independently selected from H, halogen and $C_1$-$C_6$ alkyl;

Y is —O— or —S(O)$_p$— wherein p is 0, 1 or 2; and $R^1$ is a radical of formula (IIA), (IIB), (IIC) or (IID);

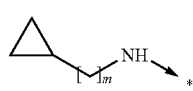
(IIA)

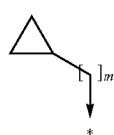
(IIB)

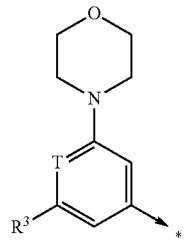
(IIC)

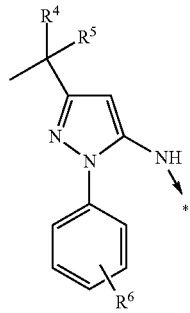
(IID)

wherein
m is 0 or 1;
T is —N or —CH;
$R^3$ is H or F;
$R^4$ is —CH$_3$; —C$_2$H$_5$; —CH$_2$OH, CH$_2$SCH$_3$; —SCH$_3$ or —SC$_2$H$_5$;
$R^5$ is —CH$_3$ or —C$_2$H$_5$;
$R^6$ is H, or represents one or more substituents, each independently selected from $C_1$-$C_6$ alkyl, hydroxy, halogen, and radicals of formulae (IIIA), (IIIB) and (IIIC):

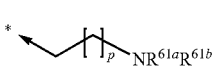
(IIIA)

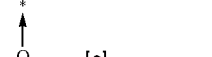
(IIIB)

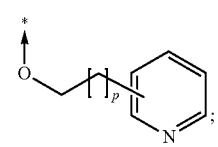
(IIIC)

wherein
$R^{61a}$ and $R^{61b}$ are independently H or $C_1$-$C_6$ alkyl, or $R^{61a}$ and $R^{61b}$ taken together with the nitrogen to which they are attached to form a 6-membered heterocyclic ring optionally containing a further heteroatom selected from N and O;
p is 1 or 2.

Currently preferred subclasses of compounds of the invention include: those wherein, in any compatible combination:
Y is —S—;
$R^{2a}$, $R^{2b}$ and $R^{2c}$ are independently selected from H, F, and Cl, for example when $R^{2a}$ is H, $R^{2b}$ is 2-chloro or 2-fluoro, and $R^{2c}$ is 6-chloro or 6-fluoro;
$R^1$ is a radical of formula (IIC) wherein $R^3$ is fluorine;
$R^1$ is a radical of formula (IIC) wherein T is —C.

In another aspect, the invention includes pharmaceutical compositions comprising a compound of the invention, together with one or more pharmaceutically acceptable carriers. Particularly preferred are compositions adapted for inhalation for pulmonary administration.

In another aspect, the invention includes the use of a compound of the invention for the treatment of diseases or conditions which benefit from inhibition of p38 MAP kinase activity. The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, asthma, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, chronic inflammatory diseases including cystic fibrosis, broncietasis and pulmonary fibrosis (Idiopathic). Efficacy is anticipated when p38 kinase inhibitors are administered either locally to the lung (for example by inhalation and intranasal delivery) or via systemic routes (for example, oral, intravenous and subcutaneous delivery).

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers may be prepared by the application of adaptation of known methods (e.g. asymmetric synthesis).

DESCRIPTION OF THE INVENTION

As used herein the term "salt" includes base addition, acid addition and ammonium salts. As briefly mentioned above compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds of the invention which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds (I) which have a basic nitrogen can also form quaternary ammonium salts with a pharmaceutically acceptable counter-ion such as ammonium, chloride, bromide, acetate, formate, p-toluenesulfonate, succinate, hemi-succinate, naphthalenebis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in several polymorphic forms and may be obtained in different crystal habits.

The compounds may also be administered in the form of prodrugs thereof. Thus certain derivatives of the compounds which may be active in their own right or may have little or no pharmacological activity themselves can, when administered into or onto the body, be converted into compounds of the invention having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, $3^{rd}$ Edition, 2002, Taylor and Francis).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985). Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

Utility

As mentioned above the compounds of the invention are p38MAPK inhibitors, and thus may have utility for the treatment of diseases or conditions which benefit from inhibition of the p38 enzyme. Such diseases and conditions are known from the literature and several have been mentioned above. However, the compounds are generally of use as anti-inflammatory agents, particularly for use in the treatment of respiratory disease. In particular, the compounds may be used in the treatment of chronic obstructive pulmonary disease (COPD), chronic bronchitis, lung fibrosis, pneumonia, acute respiratory distress syndrome (ARDS), pulmonary emphysema, or smoking-induced emphysema, intrinsic (non-allergic asthma and extrinsic (allergic) asthma, mild asthma, moderate asthma, severe asthma, steroid resistant asthma, neutrophilic asthma, bronchitic asthma, exercise induced asthma, occupational asthma and asthma induced following bacterial infection, cystic fibrosis, pulmonary fibrosis and bronchiectasis.

Compositions

As mentioned above, the compounds with which the invention is concerned are p38 kinase inhibitors, and are useful in the treatment of several diseases for example inflammatory diseases of the respiratory tract. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases. For the purpose of the invention, inhaled administration is preferred.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

However, for treatment of an inflammatory disease of the respiratory tract, compounds of the invention may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

By way of example, a composition of the invention may be prepared as a suspension for delivery from a nebuliser or as an aerosol in a liquid propellant, for example for use in a pressurised metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane)

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 µm.

In the case of an aerosol-based formulation, an example is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321). Additionally, compounds of the invention may be delivered in multi-chamber devices thus allowing for delivery of combination agents.

Combinations

Other compounds may be combined with compounds with which the invention is concerned for the prevention and treatment of inflammatory diseases, in particular respiratory diseases. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: (1) corticosteroids, such as fluticasone propionate, fluticasone furoate, mometasone furoate, beclometasone dipropionate, ciclesonide, budesonide, GSK 685698, GSK 870086, QAE 397, QMF 149, TPI-1020; (2) β2-adrenoreceptor agonists such as salbutamol, albuterol, terbutaline, fenoterol, and long acting β2-adrenoreceptor agonists such as salmeterol, indacaterol, formoterol (including formoterol fumarate), arformoterol, carmoterol, GSK 642444, GSK 159797, GSK 159802, GSK 597501, GSK 678007, AZD3199; (3) corticosteroid/long acting β2 agonist combination products such as salmeterol/fluticasone propionate (Advair/Seretide), formoterol/budesonide (Symbicort), formoterol/fluticasone propionate (Flutiform), formoterol/ciclesonide, formoterol/mometasone furoate, indacaterol/mometasone furoate, Indacaterol/QAE 397, GSK 159797/GSK 685698, GSK 159802/GSK 685698, GSK 642444/GSK 685698, GSK 159797/GSK 870086, GSK 159802/GSK 870086, GSK 642444/GSK 870086, arformoterol/ciclesonide; (4) anticholinergic agents, for example muscarinic-3 (M3) receptor antagonists such as ipratropium bromide, tiotropium bromide, Aclidinium (LAS-34273), NVA-237, GSK 233705, Darotropium, GSK 573719, GSK 961081, QAT 370, QAX 028; (5) dual pharmacology M3-anticholinergic/β2-adrenoreceptor agonists such as GSK961081; (6) leukotriene modulators, for example leukotriene antagonists such as montelukast, zafirulast or pranlukast or leukotriene biosynthesis inhibitors such as Zileuton or BAY-1005, or LTB4 antagonists such as Amelubant, or FLAP inhibitors such as GSK 2190914, AM-103; (7) phosphodiesterase-IV (PDE-IV) inhibitors (oral or inhaled), such as roflumilast, cilomilast, Oglemilast, ONO-6126, Tetomilast, Tofimilast, UK 500,001, GSK 256066; (8) antihistamines, for example selective histamine-1 (H1) receptor antagonists, such as fexofenadine, citirizine, loratidine or astemizole or dual H1/H3 receptor antagonists such as GSK 835726, GSK 1004723; (9) antitussive agents, such as codeine or dextramorphan; (10) a mucolytic, for example N acetyl cysteine or fudostein; (11) a expectorant/mucokinetic modulator, for example ambroxol, hypertonic solutions (e.g. saline or mannitol) or surfactant; (12) a peptide mucolytic, for example recombinant human deoxyribonoclease I (dornase-alfa and rhDNase) or helicidin; (13) antibiotics, for example azithromycin, tobramycin and aztreonam; (14) non-selective COX-1/COX-2 inhibitors, such as ibuprofen or ketoprofen; (15) COX-2 inhibitors, such as celecoxib and rofecoxib; (16) VLA-4 antagonists, such as those described in WO97/03094 and WO97/02289; (17) TACE inhibitors and TNF-α inhibitors, for example anti-TNF monoclonal antibodies, such as Remicade and CDP-870 and TNF receptor immunoglobulin molecules, such as Enbrel; (18) inhibitors of matrix metalloprotease, for example MMP-12; (19) human neutrophil elastase inhibitors, such as ONO-6818 or those described in WO2005/026124, WO2003/053930 and WO06/082412; (20) A2b antagonists such as those described in WO2002/42298; (21) modulators of chemokine receptor function, for example antagonists of CCR3 and CCR8; (22) compounds which modulate the action of other prostanoid receptors, for example a thromboxane $A_2$ antagonist; DP1 antagonists such as MK-0524, CRTH2 antagonists such as ODC9101 and AZD1981 and mixed DP1/CRTH2 antagonists such as AMG 009; (23) PPAR agonists including PPAR alpha agonists (such as fenofibrate), PPAR delta agonists, PPAR gamma agonists such as Pioglitazone, Rosiglitazone and Balaglitazone; (24) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (25) A2a agonists such as those described in EP1052264 and EP1241176; (26) CXCR2 or IL-8 antagonists such as SCH 527123 or GSK 656933; (27) IL-R signalling modulators such as kineret and ACZ 885; (28) MCP-1 antagonists such as ABN-912.

METHODS OF SYNTHESIS

Compounds of formula (I) can be prepared according to the following general scheme.

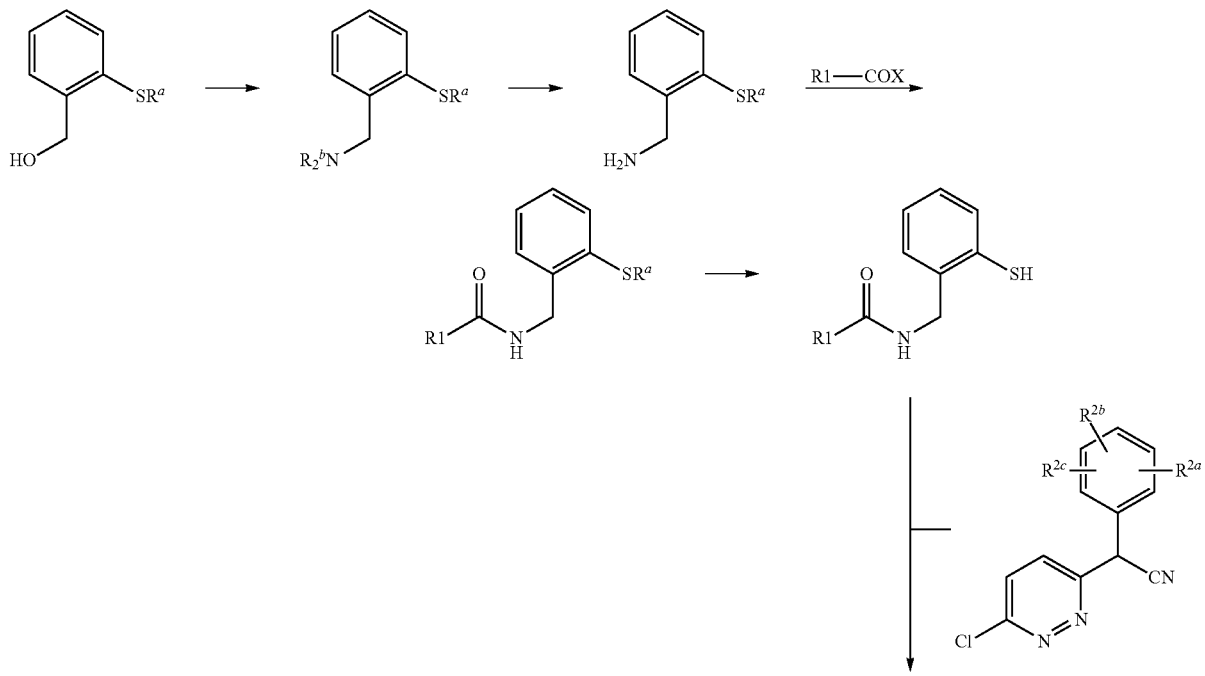

Scheme 1

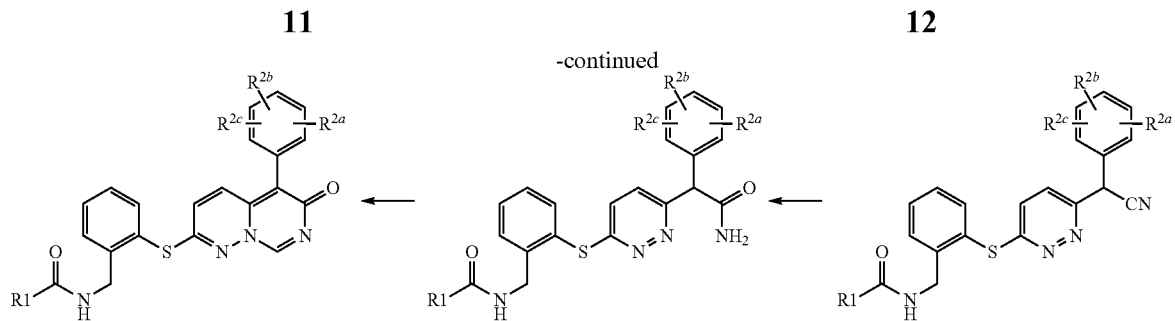

General Experimental Details

Abbreviations used in the experimental section:
DCM=dichloromethane;
DEAD=diethyl azodicarboxylate;
DIPEA=diisopropylethylamine;
DMF=N,N-dimethylformamide;
DMF-DMA=N,N-dimethylformamide dimethyl acetal;
DMSO=dimethyl sulfoxide;
EtOAc=ethyl acetate;
EtOH=ethanol;
HATU=(2-(7-aza-1H-benzotriazole-1-yl)-1,1,3,3-tetramethyluronium hexafluorophosphate);
HPLC=high performance liquid chromatography;
LCMS=liquid chromatography mass spectrometry;
MeOH=methanol; min=minutes;
RT=room temperature;
Rt=retention time;
SCX=strong cation exchange chromatography;
TFA=trifluoroacetic acid;
THF=tetrahydrofuran The nomenclature of structures was assigned using ACD/Labs version 12.0.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Where products were purified by flash column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution or use of the CombiFlash® Companion purification system or use of the Biotage SP1 purification system. Where thin layer chromatography (TLC) has been used, it refers to silica gel TLC using plates, typically 3×6 cm silica gel on aluminium foil plates with a fluorescent indicator (254 nm), (e.g. Fluka 60778). All solvents and commercial reagents were used as received.

Compounds purified by preparative HPLC were purified using a Phenomenex Luna Phenyl C6-reverse-phase column (250×21.20 mm 5 μm particle size), elution with A: water+0.1% formic acid; B: acetonitrile+0.1% formic acid. Detection—In-line UV detector set at 220 nM wavelength.

Fractions containing the required product (identified by TLC and/or LCMS analysis) were pooled, the organic fraction removed by evaporation, and the remaining aqueous fraction lyophilised, to give the final product.

The Liquid Chromatography Mass Spectroscopy (LCMS) and HPLC systems used:

Method 1

Waters Platform LC Quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line UV detector). MS ionization method—Electrospray (positive and negative ion).

Method 2

Waters ZMD quadrupole mass spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (200 μL split to MS with in-line UV detector). MS ionization method—Electrospray (positive and negative ion).

Method 3

Waters Micromass ZQ2000 with a C18-reverse-phase column (100×3.0 mm Higgins Clipeus with 5 μm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 1.0 | 95 | 5 |
| 1.00 | 1.0 | 95 | 5 |
| 15.00 | 1.0 | 5 | 95 |
| 20.00 | 1.0 | 5 | 95 |

-continued

| Gradient - Time | flow mL/min | % A | % B |
| --- | --- | --- | --- |
| 22.00 | 1.0 | 95 | 5 |
| 25.00 | 1.0 | 95 | 5 |

Detection—MS, ELS, UV (100 μL split to MS with in-line UV detector). MS ionisation method—Electrospray (positive ion)

EXAMPLE 1

N-[2-({6-[2-Amino-1-(2,6-dichlorophenyl)-2-oxoethyl]pyridazin-3-yl}sulfanyl)benzyl]-3-fluoro-5-(morpholin-4-yl)benzamide

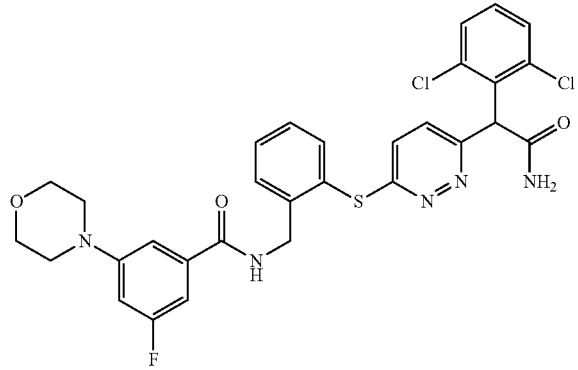 [SMILES: NC(=O)C(c1ccc(Sc2ccccc2CNC(=O)c2cc(F)cc(N3CCOCC3)c2)nn1)c1c(Cl)cccc1Cl]

a. 2-[2-(Tritylsulfanyl)benzyl]-1H-isoindole-1,3(2H)-dione

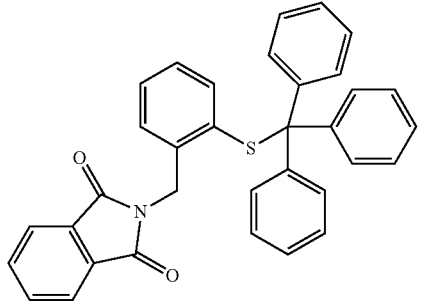 [SMILES: O=C1c2ccccc2C(=O)N1Cc1ccccc1SC(c1ccccc1)(c1ccccc1)c1ccccc1]

To a solution of (2-tritylsulfanylphenyl)-methanol (4.7 g, 12.3 mmol), phthalamide (2.29 g, 15.6 mmol) and thiphenylphosphine (4.09 g, 15.6 mmol) in THF (70 mL) at 0° C. under an argon atmosphere, was slowly added DEAD (2.4 mL, 15 mmol). The reaction mixture was stirred at RT for 30 min, then partitioned between aqueous saturated NaHCO₃ and EtOAc. The organic layer was separated, dried over MgSO₄, filtered, and the filtrate was concentrated in vacuo to afford the title compound (4.7 g, 75%) as yellow foam. ¹H NMR (300 MHz, CDCl₃): δ 7.82 (2H, m), 7.70 (2H, m), 7.38-7.33 (5H, m), 7.27-7.22 (10H, m), 7.12 (1H, dd, J 1.4, 0.5), 7.08 (1H, dt, J 1.4, 0.5), 6.96 (1H, dd, J 7.6, 1.5), 6.88 (1H, dt, J 7.6, 1.5), 4.47 (2H, s).

b. 1-[2-(Tritylsulfanyl)phenyl]methanamine

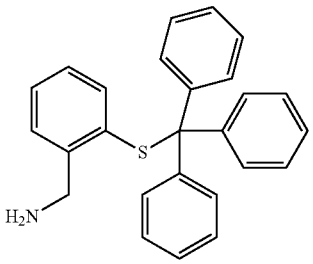 [SMILES: NCc1ccccc1SC(c1ccccc1)(c1ccccc1)c1ccccc1]

2-[2-(Tritylsulfanyl)benzyl]-1H-isoindole-1,3(2H)-dione (4.7 g, 9.19 mmol) was suspended in EtOH (150 mL) and treated with hydrazine monohydrate 65% (4.66 mL, 62 mmol). The mixture was heated under reflux for 1.5 h, cooled to RT and the precipitate was filtered. The filtrate was concentrated, triturated with EtOAc and filtered. The filtrate was concentrated under reduced pressure to afford the title compound (3.0 g, 86%) as a colourless oil. ¹H NMR (300 MHz, CDCl₃): δ 7.34-7.28 (6H, m), 7.26-7.18 (9H, m), 7.15 (2H, m), 7.10 (1H, m), 6.93-6.85 (1H, m), 3.40 (2H, s).

c. 3-Fluoro-5-(morpholin-4-yl)-N-[2-(tritylsulfanyl)benzyl]benzamide

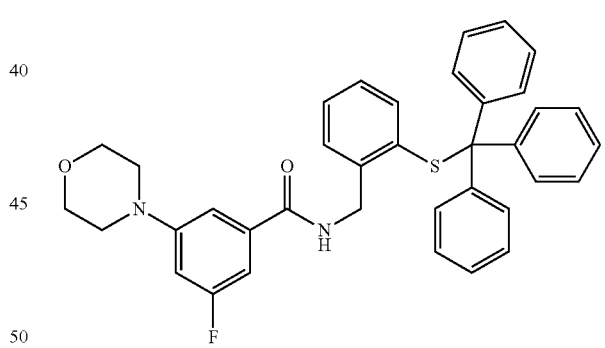

A suspension of 1-[2-(tritylsulfanyl)phenyl]methanamine (335 mg, 0.88 mmol), 3-fluoro-5-morpholin-4-yl-benzoic acid (WO2004/089929) (237 mg, 1.05 mmol) and DIPEA (0.38 mL, 2.19 mmol) in DMF (15 mL) was treated with HATU (400 mg, 1.05 mmol). The mixture was stirred at RT for 45 min, then partitioned between aqueous saturated NaHCO₃ and EtOAc. The organic layer was separated, dried over MgSO₄, filtered, and the filtrate was concentrated in vacuo to afford the title compound (quantitative) as an off-white solid. ¹H NMR (300 MHz, CDCl₃): δ 7.35-7.29 (6H, m), 7.27-7.19 (10H, m), 7.17 (2H, m), 7.10 (1H, t, J 1.7), 6.98-6.92 (1H, m), 6.73-6.64 (2H, m), 5.98 (1H, br t, J 6), 4.21 (2H, d, J 6), 3.84 (4H, t, J 4.8), 3.19 (4H, t, J 4.8).

d. 3-Fluoro-5-(morpholin-4-yl)-N-(2-sulfanylbenzyl)benzamide

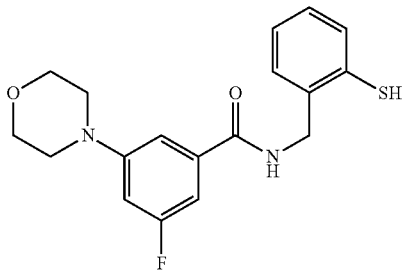 [SMILES: O=C(NCc1ccccc1S)c1cc(F)cc(N2CCOCC2)c1]

3-Fluoro-5-(morpholin-4-yl)-N-[2-(tritylsulfanyl)benzyl]benzamide (517 mg, 0.88 mmol) was treated with a solution of triethylsilane/TFA/DCM (10 mL, 1/9/10). The reaction mixture was stirred at RT for 20 min and concentrated under reduced pressure. Purification of the residue by flash column chromatography (DCM:MeOH 98:2) afforded the title compound (219 mg, 72%) as a yellow oil. $^1$H NMR (300 MHz, CDCl$_3$): δ 7.36-7.31 (2H, m), 7.21-7.15 (3H, m), 6.85 (1H, ddd, J 8.5, 2.2, 1.4), 6.69 (1H, dt, J 11.6, 2.3), 6.57 (1H, br t, J 5.7), 5.39 (1H, br s), 4.66 (2H, d, J 5.7), 3.84 (4H, t, J 4.9), 3.20 (4H, t, J 4.9).

e. N-[2-({6-[Cyano(2,6-dichlorophenyl)methyl]pyridazin-3-yl}sulfanyl)benzyl]-3-fluoro-5-(morpholin-4-yl)benzamide

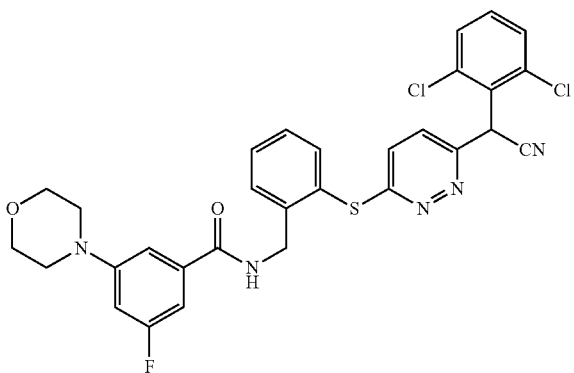 [SMILES: N#CC(c1ccc(Sc2ccccc2CNC(=O)c2cc(F)cc(N3CCOCC3)c2)nn1)c1c(Cl)cccc1Cl]

A solution of 3-fluoro-5-(morpholin-4-yl)-N-(2-sulfanylbenzyl)benzamide (80 mg, 0.23 mmol) in DMF (3 mL) was treated with sodium hydride (60% in mineral oil, 8.8 mg, 0.22 mmol). The mixture was stirred for 5 min and treated with a solution of (6-chloro-pyridazin-3-yl)-(2,6-dichloro-phenyl)-acetonitrile (63 mg, 0.21 mmol) in DMF (1 mL). The reaction mixture was heated at 100° C. for 45 min, cooled to RT and partitioned between aqueous saturated NaHCO$_3$ and EtOAc. The aqueous layer was extracted with EtOAc, the combined organic layers were dried over MgSO$_4$, filtered, and the filtrate was concentrated in vacuo. Purification by reverse phase preparative HPLC (water/acetonitrile+0.1% HCO$_2$H 50% isocratic), afforded the title compound (32 mg, 25%) as a yellow oil. LCMS (Method 3): Rt 11.77 min, m/z 608 [MH$^+$]. $^1$H NMR (400 MHz, CDCl$_3$): 7.67-7.58 (2H, m), 7.53-7.47 (1H, m), 7.45-7.32 (4H, m), 7.31-7.20 (2H, m), 7.09 (1H, t, J 1.7), 6.75 (1H, br t, J 5.6), 6.71-6.61 (2H, m), 6.33 (1H, s), 4.76 (2H, m), 3.86 (4H, t, J 4.8), 3.21 (4H, t, J 4.8).

f. N-[2-({6-[2-Amino-1-(2,6-dichlorophenyl)-2-oxoethyl]pyridazin-3-yl}sulfanyl)benzyl]-3-fluoro-5-(morpholin-4-yl)benzamide

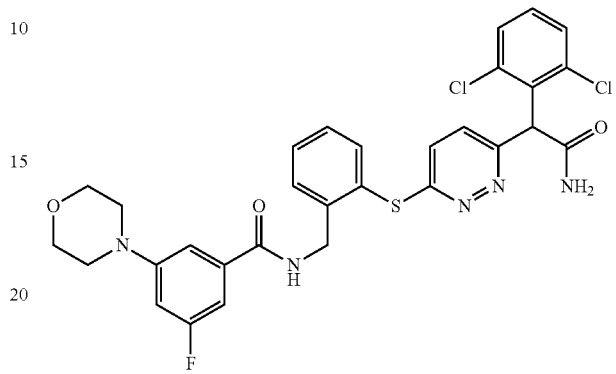

N-[2-({6-[Cyano(2,6-dichlorophenyl)methyl]pyridazin-3-yl}sulfanyl)benzyl]-3-fluoro-5-(morpholin-4-yl)benzamide (92 mg, 0.15 mmol) was treated with concentrated sulfuric acid (2 mL) and the mixture was stirred at 70° C. for 30 min. The solution was cooled to RT, quenched with ice-water and extracted into DCM. The organic layer was washed with aqueous saturated NaHCO$_3$, dried over MgSO$_4$, filtered, and the filtrate was concentrated in vacuo. Purification by flash column chromatography (DCM:MeOH from 97.3:2.7 to 95:5) afforded the title compound (63 mg, 67%) which coexists in solution as a mixture of the amide and the enol-amine. LCMS (Method 3): Rt 10.15 & 11.27 min, m/z 626 [MH$^-$]. $^1$H NMR (400 MHz, CD$_3$OD) (ratio amide/enol-amine 1:0.8): 7.65 (1H, dd, J 7.6, 1.2), 7.57-7.43 (5.4H, m), 7.42-7.37 (3.6H, m), 7.36-7.29 (3.6H, m), 7.21 (0.8H, t, J 1.8), 7.17-7.13 (2H, m), 6.99 (0.8H, ddd, J 9, 2.3, 1.4), 6.95-6.93 (1H, m), 6.85-6.80 (1.8H, m), 6.58 (0.8H, d, J 9.9), 6.15 (0.8H, d, J 9.9), 5.98 (1H, s), 4.73 (1.6H, s), 4.71 (2H, d, J 1.8), 3.82 (7.2H, t, J 4.8), 3.22-3.17 (7.2H, m).

EXAMPLE 2

N-(2-{[5-(2,6-Dichlorophenyl)-6-oxo-6H-pyrimido[1,6-b]pyridazin-2-yl]sulfanyl}benzyl)-3-fluoro-5-(morpholin-4-yl)benzamide

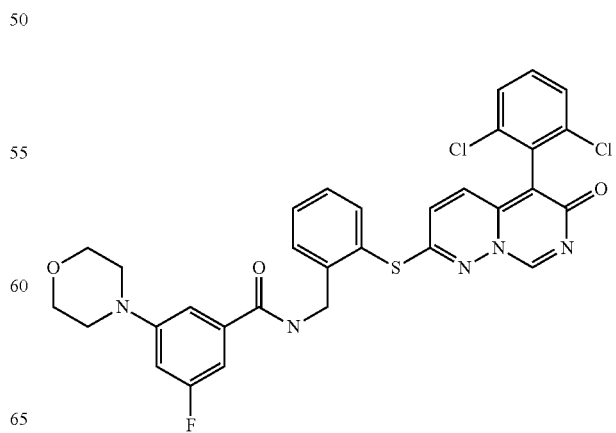

A solution of N-[2-({6-[2-amino-1-(2,6-dichlorophenyl)-2-oxoethyl]pyridazin-3-yl}sulfanyl)benzyl]-3-fluoro-5-(morpholin-4-yl)benzamide (91 mg, 0.145 mmol) in toluene (4 mL) under an argon atmosphere was treated with DMF-DMA (0.042 mL, 0.315 mmol). The mixture was heated at 100° C. for 1.75 h, then cooled to RT and the precipitate separated by filtration to afford the title compound (77 mg, 84%) as a yellow powder. LCMS (Method 3): Rt 9.8 min, m/z 636 [MH$^+$]. $^1$H NMR (400 MHz, DMSO-$d_6$): 9.01 (1H, t, J 5.7), 8.82 (1H, d, J 0.7), 7.70 (1H, dd, J 7.7, 1.2), 7.60 (2H, m), 7.58-7.52 (2H, m), 7.49 (1H, dd, J 8.9, 7.3), 7.42 (1H, td, J 7.3, 2), 7.23 (1H, br t, J 1.6), 7.04-6.98 (2H, m), 6.93-6.86 (2H, m), 4.66 (2H, d, J 5.6), 3.73 (4H, t, J 4.7), 3.17 (4H, t, J 4.7).

BIOLOGICAL ASSAYS p38 Kinase Assay

Human recombinant p38 enzyme expressed in *E. coli* and activated by incubation with MKK6 enzyme (Calbiochem #559324) is used as source of enzyme activity.

The assay is carried in high binding, clear, flat bottom 96 well assay plates which have been coated with recombinant ATF-2 (Biosource #PHF0043). Test compounds are incubated with p38 kinase for 2 h prior to initiating the kinase assay by the addition of ATP to obtain an assay concentration of 250 μM. Phosphorylation of ATF-2 is detected and quantified using an ELISA. This consists of sequential incubation in the presence of anti-phospho-ATF2, biotinylated anti-IgG and streptavidin-HRP. Incubation with an HRP chromogenic substrate (TMB) results in absorbance that is proportional to the amount of phosphorylated substrate produced. Absorbance is detected using a multiwell plate reader.

Compounds are diluted in DMSO prior to addition to assay buffer, the final DMSO concentration in the assay being 1%.

The IC$_{50}$ is defined as the concentration at which a given compound achieves 50% inhibition of control.

| Example | p38α inhibition |
|---------|-----------------|
| 1 | ++++ |
| 2 | +++ |

In the table above, p38α binding potencies (IC$_{50}$ values) are indicated as follows: <100 nM '+++'; <10 nM '++++'. All compounds tested exhibited IC$_{50}$ values <100 nM. NT = Not Tested.

The invention claimed is:

1. A compound of formula (IA) or (IB)

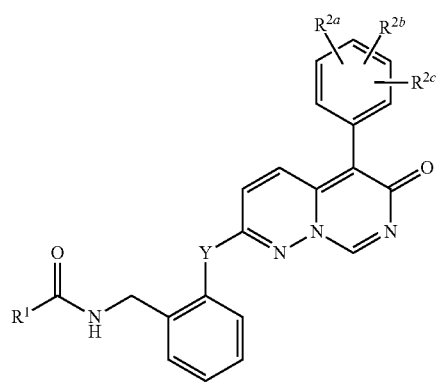

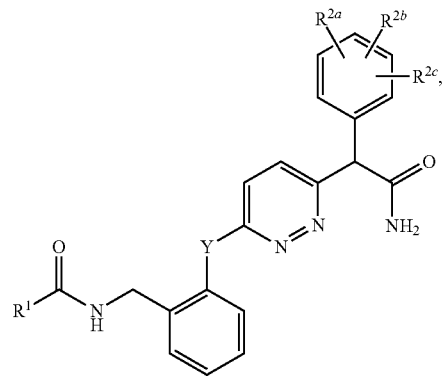

or a pharmaceutically acceptable salt thereof,
wherein:
R$^{2a}$, R$^{2b}$, and R$^{2c}$ are independently selected from H, halogen and C$_1$-C$_6$ alkyl;
Y is —O— or —S(O)$_p$— wherein p is 0, 1 or 2; and
R$^1$ is a radical of formula (IIA), (IIB), (IIC), or (IID)

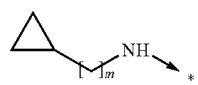

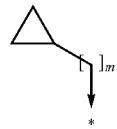

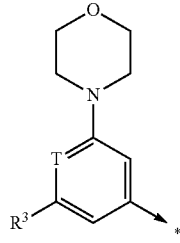

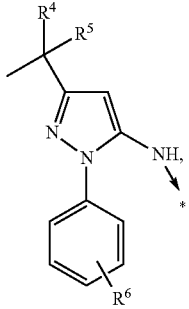

wherein
m is 0 or 1,
T is —N or —CH,
R$^3$ is H or F,
R$^4$ is —CH$_3$; —C$_2$H$_5$; —CH$_2$OH, CH$_2$SCH$_3$; —SCH$_3$, or —SC$_2$H$_5$,
R$^5$ is —CH$_3$ or —C$_2$H$_5$;
R$^6$ is H, or represents one or more substituents, each independently selected from the group consisting of a C$_1$-C$_6$ alkyl, hydroxy, a halogen, a radical of formula (IIIA), a radical of formula (IIIB), and a radical of formula (IIIC):

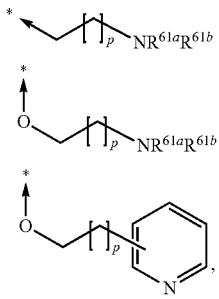

wherein
$R^{61a}$ and $R^{61b}$ are independently H or $C_1$-$C_6$ alkyl, or $R^{61a}$ and $R^{61b}$, taken together with the nitrogen to which they are attached, form a 6-membered heterocyclic ring optionally comprising a further heteroatom selected from the group consisting of N and O; and
p is 1 or 2.

2. A compound of claim 1, wherein $R^1$ is a radical of formula (IIC) wherein $R^3$ is fluorine.

3. A compound of claim 1 wherein $R^1$ is a radical of formula (IIC) wherein T is —CH.

4. A compound of claim 1, wherein Y is —S—.

5. A compound of claim 1, wherein $R^{2a}$, $R^{2b}$, and $R^{2c}$ are independently selected from the group consisting of H, F, and Cl.

6. A compound of claim 1, wherein
$R^{2a}$ is H,
$R^{2b}$ is 2-chloro or 2-fluoro, and
$R^{2c}$ is 6-chloro or 6-fluoro.

7. A pharmaceutical composition, comprising:
a compound of claim 1; and
one or more pharmaceutically acceptable carriers.

8. A composition of claim 7, which is adapted for inhalation for pulmonary administration.

9. A method of treating a disease or condition, the method comprising administering to a subject in need thereof, an effective amount of a compound of claim 1,
wherein the treating of the disease or condition benefits from an inhibition of p38 MAP kinase activity.

10. A method of claim 9, wherein the disease or condition is chronic eosinophilic pneumonia, asthma, COPD, adult respiratory distress syndrome (ARDS), exacerbation of airways hyper-reactivity consequent to other drug therapy, or airways disease that is associated with pulmonary hypertension.

11. A compound of claim 2 wherein $R^1$ is a radical of formula (IIC) wherein T is —C.

12. A compound of claim 2, wherein Y is —S—.

13. A compound of claim 3, wherein Y is —S—.

14. A compound of claim 2, wherein $R^{2a}$, $R^{2b}$, and $R^{2c}$ are independently selected from the group consisting of H, F, and Cl.

15. A compound of claim 3, wherein $R^{2a}$, $R^{2b}$, and $R^{2c}$ are independently selected from the group consisting of H, F, and Cl.

16. A compound of claim 4, wherein $R^{2a}$, $R^{2b}$, and $R^{2c}$ are independently selected from the group consisting of H, F, and Cl.

17. A compound of claim 6, wherein $R^{2b}$ is 2-chloro.

18. A compound of claim 6, wherein $R^{2b}$ is 2-fluoro.

19. A compound of claim 6, wherein $R^{2c}$ is 6-chloro.

20. A compound of claim 6, wherein $R^{2c}$ is 6-fluoro.

* * * * *